US010226221B2

(12) United States Patent
Matthews

(10) Patent No.: US 10,226,221 B2
(45) Date of Patent: Mar. 12, 2019

(54) MEDICAL IMAGE PROCESSING METHOD AND APPARATUS

(71) Applicant: Toshiba Medical Systems Corporation, Otawara-shi (JP)

(72) Inventor: James Matthews, Edinburgh (GB)

(73) Assignee: TOSHIBA MEDICAL SYSTEMS CORPORATION, Otawara-shi (JP)

( * ) Notice: Subject to any disclaimer, the term of this patent is extended or adjusted under 35 U.S.C. 154(b) by 99 days.

(21) Appl. No.: 15/251,162

(22) Filed: Aug. 30, 2016

(65) Prior Publication Data

US 2018/0055460 A1     Mar. 1, 2018

(51) Int. Cl.
*A61B 6/03*     (2006.01)
*G06T 7/00*     (2017.01)
(Continued)

(52) U.S. Cl.
CPC .............. *A61B 6/035* (2013.01); *A61B 6/503* (2013.01); *A61B 6/527* (2013.01); *G06T 7/0012* (2013.01);
(Continued)

(58) Field of Classification Search
CPC ..... A61B 34/10; A61B 6/5235; A61B 6/5247; A61B 8/52; A61B 8/4461; A61B 8/4483;
(Continued)

(56) References Cited

U.S. PATENT DOCUMENTS 6,381,349 B1 * 4/2002 Zeng ...................... G06T 11/005
382/128
7,778,392 B1 * 8/2010 Berman ................. A61B 6/032
378/210

(Continued)

FOREIGN PATENT DOCUMENTS

AU    2003243469 A1   12/2003
JP    2005-529658 A   10/2005
(Continued)

OTHER PUBLICATIONS

Terry Peters, "CT Image Reconstruction," Robarts Research Institute, Jul. 18, 2002, URL: https://www.aapm.org/meetings/02AM/pdf/8372-23331.pdf.

(Continued)

*Primary Examiner* — Jingge Wu
(74) *Attorney, Agent, or Firm* — Oblon, McClelland, Maier & Neustadt, L.L.P.

(57) ABSTRACT

A medical imaging data processing apparatus comprises processing circuitry configured to obtain a first imaging data set comprising a set of pixels or voxels, the first imaging data set being reconstructed from first measurement data representative of measurements of a measurement volume obtained by relative rotation of a medical scanner and the measurement volume by a first range of angles during a first scanning time period; obtain a second imaging data set comprising a set of pixels or voxels, the second imaging data set being reconstructed from second measurement data representative of measurements of the measurement volume obtained by relative rotation of the medical scanner and the measurement volume by a second range of angles during a second scanning time period, wherein the second scanning time period overlaps the first scanning time period such that some angles are included in both the first range of angles and the second range of angles; transform the first imaging data set to obtain a first transformed data set that is representative of the first measurement data as a function of at least one of angle or time; transform the second imaging data set to obtain a second transformed data set that is representative of the second measurement data as a function of at least one of angle or time; and determine at least one angle of the first range of angles and/or second range of angles based on differences between the first transformed data set and second transformed data set.

20 Claims, 4 Drawing Sheets

(51) Int. Cl.
*G06T 7/20* (2017.01)
*A61B 6/00* (2006.01)

(52) U.S. Cl.
CPC .... *G06T 7/206* (2013.01); *G06T 2207/10081* (2013.01); *G06T 2207/10088* (2013.01); *G06T 2207/10104* (2013.01); *G06T 2207/10108* (2013.01); *G06T 2207/10116* (2013.01); *G06T 2207/10132* (2013.01); *G06T 2207/20056* (2013.01); *G06T 2207/20224* (2013.01)

(58) Field of Classification Search
CPC ............... A61B 8/5238; A61B 8/5253; A61B 618/5261; G06T 2207/30004; G06T 3/0056; G06T 7/00; G06T 7/0002
See application file for complete search history.

(56) References Cited

U.S. PATENT DOCUMENTS

| | | | |
|---|---|---|---|
| 9,008,401 B1 | 4/2015 | Katsevich et al. | |
| 9,173,629 B2* | 11/2015 | Osumi | A61B 8/00 |
| 9,224,216 B2 | 12/2015 | Zamyatin et al. | |
| 2004/0114146 A1* | 6/2004 | Willis | A61B 8/12 356/446 |
| 2007/0010731 A1 | 1/2007 | Mistretta | |
| 2007/0055159 A1* | 3/2007 | Wang | A61B 8/0825 600/443 |
| 2007/0217666 A1* | 9/2007 | Gal | G01T 1/1642 382/131 |
| 2009/0046275 A1* | 2/2009 | Jefferson | G01N 21/553 356/73 |
| 2011/0188723 A1* | 8/2011 | Bruder | A61B 6/032 382/131 |
| 2013/0094740 A1* | 4/2013 | Vandenberghe | A61B 6/14 382/131 |
| 2014/0140469 A1* | 5/2014 | Carmi | G01N 23/046 378/9 |
| 2015/0036902 A1 | 2/2015 | Zamyatin et al. | |
| 2016/0110874 A1 | 4/2016 | Matthews et al. | |
| 2016/0189374 A1* | 6/2016 | Woodsum | G06K 9/522 382/131 |
| 2017/0325709 A1* | 11/2017 | Nayak | A61B 5/055 |

FOREIGN PATENT DOCUMENTS

| | | |
|---|---|---|
| JP | 2009-500114 A | 1/2009 |
| JP | 2012-11111 A | 1/2012 |
| JP | 2015-29913 A | 2/2015 |
| WO | WO 2007/008532 A1 | 1/2007 |

OTHER PUBLICATIONS

QiulinTang, et al., "A combined local and global motion estimation and compensation method for cardia CT," Proc. SPIE 9033, Medical Imaging 2014: Physics of Medical Imaging, 903304, Mar. 19, 2014, 6 pages.

Luis C. Maas, et al., "Decoupled automated Rotational and Translational Registration for Functional MRI Time Series Data: The DART Registration Algorithm," Magnetic Resonance in Medicine, (1997), pp. 131-139.

* cited by examiner

MEDICAL IMAGE PROCESSING METHOD AND APPARATUS

FIELD

Embodiments described herein relate generally to a method of, and apparatus for, obtaining at least one rotation angle from medical imaging data, for example obtaining at least one CT gantry rotation angle from two or more medical imaging data sets.

BACKGROUND

Image quality in CT scans of the heart may be affected by heart motion. Motion of the heart within the duration of a cardiac CT scan capture may result in the presence of motion artifacts in images derived from the cardiac CT scan.

Some methods for motion compensation in CT are known in which motion (for example, cardiac motion) is estimated based on three reconstruction volumes at close time points within a single rotation of a scanner. For example, in a scanner having a rotation time of 275 ms, three reconstruction volumes may be obtained at around 70 ms apart and motion may be estimated based on those reconstruction volumes. It is known to perform motion compensated reconstruction, in which a new reconstruction volume with reduced artifacts is obtained using the estimated motion.

In some circumstances, such motion compensation methods may be tightly integrated into a CT scanner system or other scanner apparatus and may use information obtained directly from the scanner itself but that is not available from standard DICOM tags. Such information may be not available from, or stored with, reconstructed imaging data. Therefore, it can sometimes be difficult to apply motion compensation methods to stored imaging data or data processed remotely from the scanner system itself, or data processed at a later time after completion of the scan measurements.

BRIEF DESCRIPTION OF THE DRAWINGS

Embodiments are now described, by way of non-limiting example, and are illustrated in the following figures, in which.

DETAILED DESCRIPTION

Figure 1:
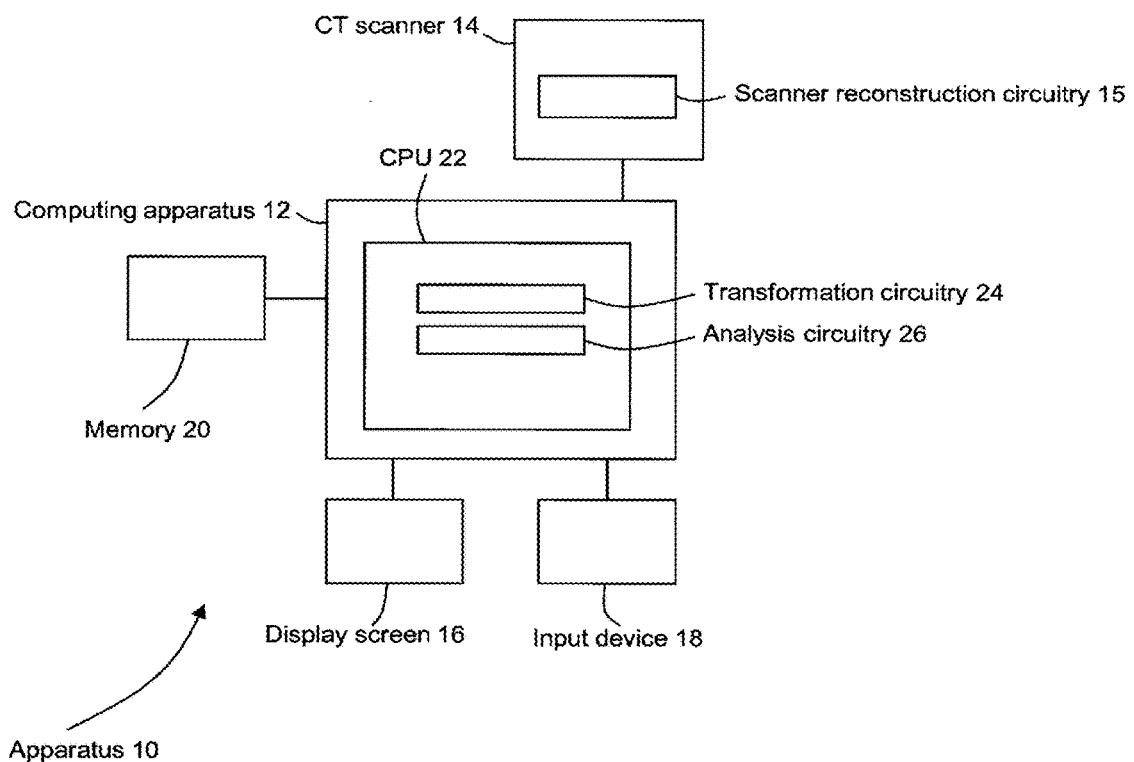
FIG. 1 is a schematic illustration of an apparatus according to an embodiment.

Certain embodiments provide a medical imaging data processing apparatus comprising processing circuitry configured to obtain a first imaging data set comprising a set of pixels or voxels, the first imaging data set being reconstructed from first measurement data representative of measurements of a measurement volume obtained by relative rotation of a medical scanner and the measurement volume by a first range of angles during a first scanning time period; obtain a second imaging data set comprising a set of pixels or voxels, the second imaging data set being reconstructed from second measurement data representative of measurements of the measurement volume obtained by relative rotation of the medical scanner and the measurement volume by a second range of angles during a second scanning time period, wherein the second scanning time period overlaps the first scanning time period such that some angles are included in both the first range of angles and the second range of angles; transform the first imaging data set to obtain a first transformed data set that is representative of the first measurement data as a function of at least one of angle or time; transform the second imaging data set to obtain a second transformed data set that is representative of the second measurement data as a function of at least one of angle or time; and determine at least one angle of the first range of angles and/or second range of angles based on differences between the first transformed data set and second transformed data set.

Certain embodiments provide a medical imaging data processing method comprising: obtaining a first imaging data set comprising a set of pixels or voxels, the first imaging data set being reconstructed from first measurement data representative of measurements of a measurement volume obtained by relative rotation of a medical scanner and the measurement volume by a first range of angles during a first scanning time period; obtaining a second imaging data set comprising a set of pixels or voxels, the second imaging data set being reconstructed from second measurement data representative of measurements of the measurement volume obtained by relative rotation of the medical scanner and the measurement volume by a second range of angles during a second scanning time period, wherein the second scanning time period overlaps the first scanning time period such that some angles are included in both the first range of angles and the second range of angles; transforming the first imaging data set to obtain a first transformed data set that is representative of the first measurement data as a function of at least one of angle or time; transforming the second imaging data set to obtain a second transformed data set that is representative of the second measurement data as a function of at least one of angle or time; and determining at least one angle of the first range of angles and/or second range of angles based on differences between the first transformed data set and second transformed data set.

An imaging data processing apparatus 10 according to an embodiment is illustrated schematically in FIG. 1. The imaging data processing apparatus 10 comprises a computing apparatus 12, for example, a personal computer (PC) or workstation, which is connected to a CT scanner 14, one or more display screens 16 and an input device or devices 18, such as a computer keyboard, mouse or trackball.

Although in the present embodiment the computing apparatus 12 is connected to the CT scanner 14, in other embodiments the computing apparatus 12 is a workstation that is not connected to a CT scanner 14. The computing apparatus 12 may be a workstation that is configured to process stored CT data, for example CT data that has been stored in a Picture Archiving and Communication System (PACS).

The CT scanner 14 may be any CT scanner that is configured to obtain two-dimensional or three-dimensional CT scan data that is representative of a region of a patient or other subject. In alternative embodiments, the CT scanner 14 may be replaced or supplemented by a scanner in any other imaging modality, for example a cone-beam CT scanner, MRI (magnetic resonance imaging) scanner, X-ray scanner, PET (positron emission tomography) scanner, SPECT (single photon emission computed tomography) scanner, or ultrasound scanner.

In the present embodiment, the region for which scan data is obtained is an anatomical region of a patient, comprising the heart. In other embodiments, the region may be any appropriate region. For example, the region may comprise any appropriate vessel (for example, the coronary arteries) or organ (for example, the lung or liver). The region of the patient that is scanned may be referred to as a measurement volume.

The CT scanner 14 is configured to scan the region of the patient using an X-ray source and receiver mounted on a gantry. The gantry performs a full 360° rotation around the patient in a rotation time, which in the present embodiment is 275 ms. In some circumstances, a full rotation may be completed within a single heartbeat of the patient.

During each rotation, the receiver generates a plurality of subsets of CT scan data, each subset corresponding to a different time during the rotation and therefore to a different angle of rotation. Each subset of data may be representative of an attenuation of X-rays passing from the source through the patient to the receiver at a respective angle of rotation. Each subset of data may comprise, for example, voltage data.

In the present embodiment, each full rotation around the patient provides CT scan data that is representative of an axial slice of the region of the patient. In other embodiments, the CT scanner 14 may be a spiral CT scanner providing spiral CT scan data that is capable of being processed to obtain axial slice data.

In the description below, the term scan data set (for example, CT scan data set) is used to refer to raw (unreconstructed) data. CT scan data may be representative of measurements obtained by the scanner during a CT scan, for example voltage data that is obtained by the receiver at each of a plurality of angles of rotation. A CT scan data set may comprise data that is representative of one or more axial slices. In some circumstances, a CT scan data set may be referred to as a sinogram.

In the present embodiment, CT scanner 14 comprises scanner reconstruction circuitry 15 that is configured to reconstruct CT scan data to obtain imaging data. It is a principle of CT scanning that CT scan data for a plurality of angles of rotation may be reconstructed to obtain imaging data comprising a plurality of pixels or voxels, each pixel or voxel being representative of a corresponding location in the measurement volume. Each pixel or voxel may comprise or be associated with a respective intensity value that is, for example, representative of attenuation of X-rays at the corresponding location in space, for example the corresponding location in the measurement volume.

In the description below, the term imaging data set is used to refer to reconstructed data. An imaging data set may be used to obtain an image of the measurement volume, for example for display.

In the present embodiment, the CT scanner 14 reconstructs the CT data to obtain imaging data by using filtered back-projection. In other embodiments, any suitable reconstruction method may be used.

Taking the example of a single axial slice, CT scan data for that axial slice is obtained during 360° of rotation of the gantry. An imaging data set that is a full reconstruction of the axial slice may be obtained by using CT scan data obtained during 180° of rotation of the gantry. It is therefore possible to obtain several full reconstructions of the axial slice, with each full reconstruction using CT scan data from a different 180° (or more) of gantry rotation angles.

In the present embodiment, the scanner reconstruction circuitry 15 is configured to reconstruct, for each axial slice, several imaging data sets, each imaging data set being reconstructed from CT scan data for a different range of gantry rotation angles.

Each imaging data set is reconstructed from CT scan data for a different 180° of gantry rotation angles. Therefore, the ranges of gantry rotation angles used for different reconstructions overlap. For example, for a given slice, the scanner reconstruction circuitry 15 may reconstruct a first imaging data set using CT scan data for a first range of gantry angles from 0° to 180° and a second imaging data set using CT scan data for a second range of gantry angles from 90° to 270°. In reconstructing each imaging data set from CT scan data, the scanner reconstruction circuitry 15 makes use of information regarding the gantry rotation angles.

If no motion were to occur in the measurement volume during rotation, it may be expected that each of the imaging data sets may be substantially identical. However, the presence of motion may cause differences between the imaging data sets reconstructed from different angular ranges (and therefore representative of different times). For example, a shape and/or position of the heart may change between the scanning time period for the first imaging data set and the scanning time period for the second imaging data set.

Imaging data sets that are output by the CT scanner 14 do not generally include data relating to the range of gantry angles of the CT scan data from which they were reconstructed. Therefore, in some circumstances, it may not be possible for a user receiving an imaging data set (for example, a user receiving the imaging data set as a DICOM file) to determine the range of gantry angles from which that imaging data set was reconstructed. For example, a user consulting a DICOM file for an imaging data set may not be able to determine from the DICOM file whether that imaging data set has been reconstructed from a range of gantry rotation angles from 0° to 180° or a range of gantry rotation angles from 90° to 270°.

A plurality of imaging data sets output by the CT scanner 14 are stored in memory 20 and subsequently provided to computing apparatus 12. Each of the imaging data sets comprises a respective full reconstruction of one or more axial slices. Each of the imaging data sets was reconstructed using CT scan data for a different range of gantry rotation angles. The imaging data sets are stored without any information regarding the gantry rotation angles of the CT scan data from which each imaging data set is reconstructed.

In an alternative embodiment, imaging data sets are supplied from a remote data store (not shown) which may form part of a PACS. The memory 20 or remote data store may comprise any suitable form of memory storage. The imaging data sets are provided from the remote data store without any information regarding the gantry rotation angles of the CT scan data from which each imaging data set is reconstructed.

Computing apparatus 12 provides a processing resource for automatically or semi-automatically processing imaging data sets, and comprises a central processing unit (CPU) 22. In the present embodiment, the computing apparatus 12 includes transformation circuitry 24 and analysis circuitry 26.

In the present embodiment, the transformation circuitry 24 and analysis circuitry 26 are each implemented in computing apparatus 12 by means of a computer program having computer-readable instructions that are executable to perform the method of the embodiment. For example, the transformation circuitry 24 and analysis circuitry 26 may each be implemented as a respective computer program or algorithm that is executable by the computing apparatus 12, for example by the CPU 22. However, in other embodiments, the various units may be implemented as one or more ASICs (application specific integrated circuits) or FPGAs (field programmable gate arrays).

The computing apparatus 12 also includes a hard drive and other components of a PC including RAM, ROM, a data bus, an operating system including various device drivers, and hardware devices including a graphics card. Such components are not shown in FIG. 1 for clarity.

The system of FIG. 1 is configured to perform the method of an embodiment as described below with reference to FIG. 2, in which imaging data sets are processed to obtain information about the gantry rotation angles at which that CT data from which they are reconstructed was acquired. Such angular information may be subsequently used, for example, in methods of motion estimation or motion compensation.

Figure 2:
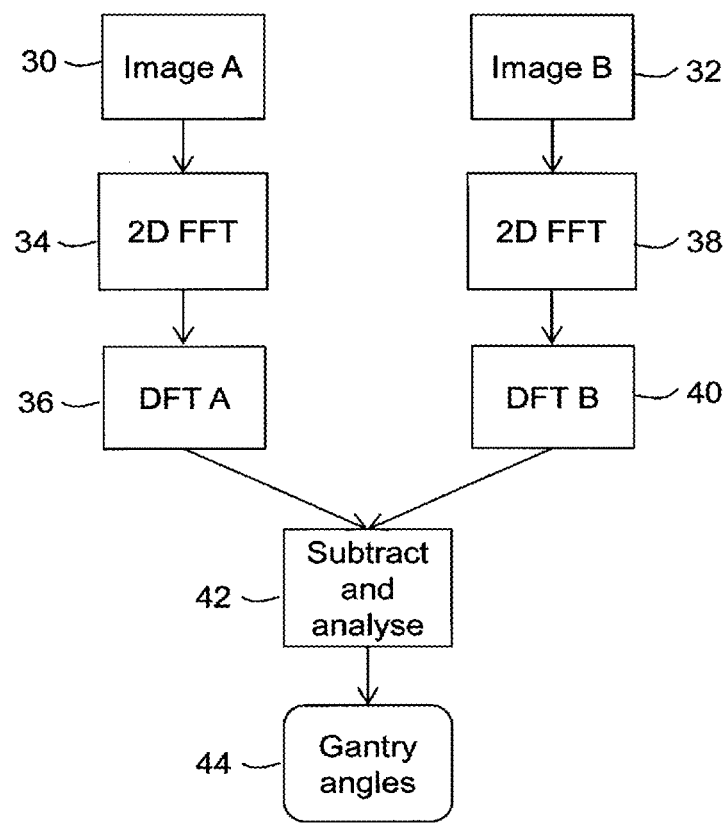
FIG. 2 is a flow chart illustrating in overview a method of an embodiment.

At stage 30 of the process of FIG. 2, the transformation circuitry 24 receives a first imaging data set from the CT scanner 14 or from a data store. The transformation circuitry 24 does not receive any information about the range of gantry rotation angles of the CT scan data from which the first imaging data set was reconstructed.

In the present embodiment, the first imaging data set comprises two-dimensional imaging data that is representative of an axial slice of a patient. Each voxel of the first imaging data set may be considered to correspond to a respective pixel of a two-dimensional image A of the axial slice. In other embodiments, the first imaging data set comprises three-dimensional imaging data, for example 3D image data that may be projected to form a two-dimensional image A. The first imaging data set may be representative of a plurality of axial slices.

At stage 32 of the process of FIG. 2, the transformation circuitry 24 receives a second imaging data set from the CT scanner 14 or data store. The transformation circuitry 24 does not receive any information about the range of gantry rotation angles of the CT scan data from which the second imaging data set was reconstructed.

In the present embodiment, the second imaging data set comprises two-dimensional imaging data that is representative of the same axial slice of the patient as the first imaging data set. Each voxel of the second imaging data set may be considered to correspond to a respective pixel of a two-dimensional image B of the axial slice. In other embodiments, the second imaging data set comprises three-dimensional imaging data that is representative of the same three-dimensional region as the first imaging data set. The second imaging data set may be representative of a plurality of axial slices.

The second imaging data set is representative of the same anatomical region of the same patient as the first imaging data set, but is reconstructed from imaging data acquired at different times. The first imaging data set is reconstructed from measurements acquired during a first scanning time period, during which the gantry rotated through a first range of gantry rotation angles. The second imaging data set is reconstructed from measurements acquired during a second scanning time period, during which the gantry rotated through a second range of gantry rotation angles. The second scanning time period overlaps with the first scanning time period. Therefore, the second range of gantry rotation angles overlaps with the first range of gantry rotation angles. Measurements for gantry angles obtained in the overlap between the first scanning time period and second scanning time period are used in the reconstruction of both the first imaging data set and the second imaging data set.

Angles that are part of both the first range of gantry rotation angles and the second range of gantry rotation angles may be referred to as overlapping angles. Angles that are part of the first range of gantry rotation angles and not part of the second range of gantry rotation angles, or angles that are part of the second range of gantry rotation angles and not part of the first range of gantry rotation angles, may be referred to as non-overlapping angles.

Since the computing apparatus 12 does not at this stage have access to information (for example, DICOM information) about the gantry rotation angles used in reconstructing each of the first imaging data set and second imaging data set, the computing apparatus 12 processes the first imaging data set and second imaging data set to obtain an estimate of at least one of the gantry rotation angles.

At stage 34, the transformation circuitry 24 performs a two-dimensional fast Fourier transform (2D FFT) of the first imaging data set to obtain a discrete Fourier transform 36 (DFT A) of the first imaging data set. In other embodiments, any method of implementing a discrete Fourier transform may be used, which may or may not be a fast Fourier transform. In some embodiments, direct calculation of the discrete Fourier transform is used.

In other embodiments, any suitable transformation may be used. Several related specializations and generalizations of the Fourier transform exist. In some embodiments, one of those specializations or generalizations may be used in place of the Fourier transformation. In some embodiments, the transformation comprises, for example, a number-theoretic transform (NTT), a discrete weighted transform (DWT), or a Chirp Z-transform.

The transformation circuitry 24 passes DFT A to the analysis circuitry 26.

The transformed first imaging data set, DFT A, comprises a plurality of elements in a Fourier transform space, each with an associated magnitude. The elements may be described as pixels. An intensity of each pixel may be representative of a magnitude of a Fourier transform coefficient represented by that pixel. The transformed data set may be representative of the CT scan data as a function of at least one of angle or time, for example angle between the scanner and the measurement volume. Some of the low frequency information in the original measurement may be lost during reconstruction (for example, there may be redundancy in the raw data, which is averaged out when creating the reconstructed image). However, most of the detail of the CT scan data may be present and represented in the transformed data set.

As a result of the central slice theorem (also known as the projection-slice theorem or the Fourier slice theorem), if a radial line is drawn through the origin of the transformed first imaging data set at an angle $\phi$, pixels on that radial line may be considered to correspond to CT scan data obtained at gantry angle $\phi$ or at gantry angle $\phi+180°$. The Fourier transformed first data set, DFT A, has a fixed origin.

Although in the description below we have referred to pixels on a line through the transformed imaging data set at angle $\phi$ as corresponding to CT scan data obtained at gantry angle $\phi$, in some embodiments the term gantry angle is used to refer to the angle of a line from the source (for example, X-ray tube) to the centre of a detector (for example, X-ray receiver). The corresponding line of sinogram data is orthogonal to the line from the source to the centre of the detector. So a line through the transformed imaging data set at an angle $\phi$ may correspond to a gantry angle of $\phi+90°$ or $\phi-90°$.

At stage 38, the transformation circuitry 24 performs a two-dimensional fast Fourier transform of the second imaging data set to obtain a discrete Fourier transform 40 (DFT B) of the first imaging data set. In other embodiments, any suitable transformation may be used to transform both the first imaging data set and the second imaging data set. The transformation circuitry 24 passes DFT B to the analysis circuitry 26.

At stage 42, the analysis circuitry 26 subtracts DFT A and DFT B to obtain a difference data set. In other embodiments, any method of obtaining a difference between DFT A and DFT B may be used. Differences between DFT A and DFT B may be expressed in any suitable format. Any suitable method of analysing difference data may be used.

In the present embodiment, the difference data set comprises a plurality of pixels corresponding to the plurality of pixels of each of DFT A and DFT B. An intensity of each of the plurality of pixels in the difference data set is representative of a magnitude of the difference between the intensity for that pixel in DFT A and the intensity of that pixel in DFT B. If the intensity of a pixel is substantially the same in DFT A as in DFT B, the intensity of that pixel in the difference data set is low. If the intensity of a pixel is different in DFT A from in DFT B, the intensity of that pixel in the difference data set is higher.

Figure 3:
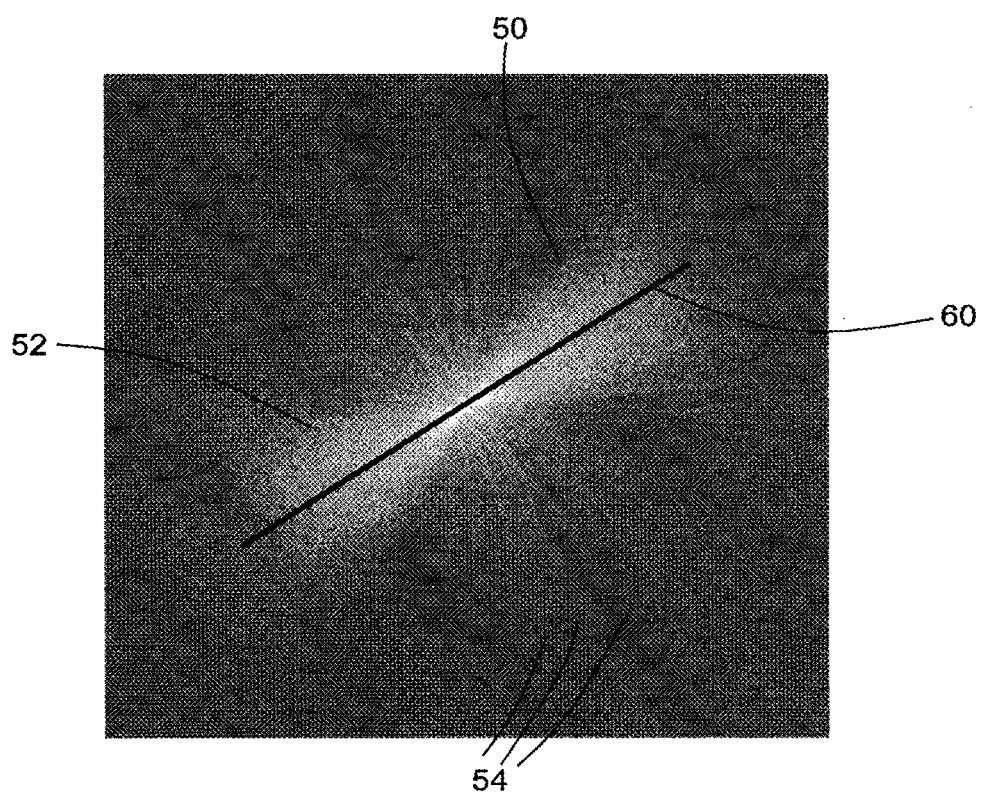
FIG. 3 is a schematic illustration of a difference of Fourier transformations of two input images.

FIG. 3 shows an image of a difference data set obtained by subtracting a DFT of a first imaging data set and a DFT of a second imaging data set, where the first imaging data set and second imaging data set are sets of two-dimensional imaging data (for example, axial slice data) that are obtained for the same anatomical region using CT data from different, overlapping ranges of gantry angles.

Processes below that are described as being performed on a difference image (for example, the difference image of FIG. 3) may in practice be performed on the difference data set, for example without an image of the difference data set being rendered. For example, where drawing a line through the difference image is described, the analysis circuitry 26 may in practice select pixels of the difference data set that, if displayed, would fall on a line across the difference image. Similarly, processes performed on the difference data set may be described in terms as if they were performed on an image (for example, drawing a line or circle on the difference data set or selecting a region of the difference data set).

Pixels of the difference data set that appear as bright pixels in the image of FIG. 3 are pixels where there is a difference between the intensity of that pixel in DFT A and the intensity of that pixel in DFT B. Pixels of the difference data set that appear dark in FIG. 3 are pixels where there is little or no difference between the intensity of that pixel in DFT A and the intensity of that pixel in DFT B.

Consider a radial line through the difference data set at an angle $\phi_1$ corresponding to a gantry angle $\phi_1$ from which CT scan data was included in both the reconstruction of the first imaging data set and the reconstruction of the second imaging data set (i.e. an angle $\phi_1$ that lies within the overlap of the first range of gantry rotation angles and the second range of gantry rotation angles).

Since the same CT scan data was used for angle $\phi_1$ in the first imaging data set as was used in the second imaging data set, pixels on a radial line through DFT A at angle $\phi_1$ may be expected to be substantially the same as pixels on a radial line through DFT B at angle $\phi_1$. Therefore, pixels on a radial line through the difference data set at angle $\phi_1$ may be expected to be dark (indicating low or no difference between the transformed data sets).

On the other hand, consider a radial line through the difference data set at an angle $\phi_2$ corresponding to a gantry angle $\phi_2$ from which CT scan data was included in the reconstruction of the first imaging data set and not the second imaging data set (or included in the reconstruction of the second imaging data set and not the first data set).

As an example, the first imaging data set may include data from gantry angle $\phi=10°$ and the second imaging data set may not include data from gantry angle $\phi=10°$ but may include data from gantry angle $\phi=190°$. In this example, the data obtained at gantry angle $\phi=190°$ is obtained at a later time than the data obtained at gantry angle $\phi=10°$. It is possible that there may have been motion in the anatomical region between the acquisition of data at $\phi=10°$ and the acquisition of data at $\phi=190°$.

Acquiring data from opposite directions (for example from $\phi=190°$ instead of $\phi=10°$) may give different results due to beam hardening and/or due to any effects other than simple attenuation. For example, different results may arise due to different scatter, which may often be seen in metal artifacts. Data acquired from opposite directions may also be different because they are different samples, and any noise captured may be different.

Pixels on a radial line through DFT A at angle $\phi_2$ may be expected to be different from pixels on a radial line through DFT B at angle $\phi_2$. Pixels on a radial line through the difference data set at angle $\phi_2$ may be expected to be bright.

In some embodiments, motion occurs between the acquisition of data at opposite angles (for example, between the acquisition of data at $\phi=10°$ and the acquisition of data at $\phi=190°$). In other embodiments, no motion occurs, or only minor motion occurs. Differences due to noise may be sufficient to observe a bright line in the difference data set even if there is no motion, or only minor motion. A small amount of motion may cause a large difference in the phase of the Fourier transforms.

In practice, the CT scan data may be processed before or during reconstruction. For example, filtering or noise reduction may be applied to the CT scan data. It may therefore be the case that even for angles $\phi$ that were used in the reconstruction of both imaging data sets, there may be some difference in the transformed imaging data sets. However, such differences may be expected to be less than the differences between angles $\phi$ for which different CT scan data was used in the reconstruction of each imaging data set. Differences due to filtering or noise reduction may result in small bright features on the difference data set (for example, bright lines or individual bright pixels) whereas a range of non-overlapping angles may appear in the difference data set as a large bright region.

In the image of FIG. 3, two bright fan-shaped regions 50, 52 are visible. The bright fan-shaped regions 50, 52 correspond to non-overlapping angles (angles for which data used in the reconstruction of one of the first imaging data set and second imaging data set is not used in the reconstruction of the other of the first imaging data set and second imaging data set).

In FIG. 3, there are also some lines of brightness 54 that are not part of the bright fan-shaped regions 50, 52. The lines of brightness may be considered to be orthogonal to a range of angles of the fan-shaped regions 50, 52. These lines of brightness may be due to processing that is applied to the CT scan data before reconstruction, or in the reconstruction of the imaging data sets, for example filtering or noise reduction. Some noise in the image of FIG. 3 may also be due to processing before or after reconstruction.

At stage 44 of the process of FIG. 2, the analysis circuitry 26 analyses the difference data set to estimate at least one gantry rotation angle. In the present embodiment, the analysis circuitry 26 analyses the difference data set to estimate a midpoint of a range of non-overlapping angles (angles for which data used in the reconstruction of one of the first imaging data set and second imaging data set was not used in the reconstruction of the other of the first imaging data set and second imaging data set). For example, in the example of FIG. 3, the analysis circuitry may estimate a midpoint of a range of non-overlapping angles corresponding to bright region 50 and/or a midpoint of a range of non-overlapping angles corresponding to bright region 52.

In the present embodiment, the analysis circuitry 26 obtains the magnitude of each pixel of the difference data set, and uses the magnitude of the pixels to obtain the midpoint of the non-overlapping regions. Since each imaging data set is reconstructed from a respective 180° of rotation, non-overlapping region 50 is offset from non-overlapping region 52 by 180°. A single radial line on FIG. 3 can be used to obtain the midpoint of both non-overlapping regions 50, 52.

In some embodiments, the analysis circuitry 26 applies a logarithm operator to the difference data set, for example to make the difference data set more suitable for display. The logarithm operator replaces each pixel value x with log (1+|x|). The replacement of each pixel value x with log (1+|x|) compresses the dynamic range of the difference data set image so that it may be easier to see patterns in it.

The applying of the logarithm operator may decrease the brightness of a central region of the difference data set relative to the rest of the difference data set. If the brightness of the central region is decreased, a viewer of an image rendered from the difference data set may be able to see features of the difference data set more easily, for example to see the bright fan-shaped regions 50, 52.

In other embodiments, no logarithm operator may be used. In some embodiments, a different type of transform may be applied to the difference data set instead of or in addition to the logarithm operator. The difference data set may be processed using any method for processing Fourier transform images for visual presentation.

In the present embodiment, the analysis circuitry 26 defines a set of radial lines, each of which passes through the centre of the difference data set at a respective angle ϕ. For each of the radial lines, the analysis circuitry determines a sum of squares of the magnitude of the pixels of the difference data set along that radial line. The analysis circuitry 26 selects the one of the radial lines for which the sum of squares is largest (which may be considered to be the radial line having the brightest pixels). The analysis circuitry uses the selected radial line to obtain an estimate of the midpoint of each of the non-overlapping ranges of angles.

An example of a selected radial line 60 is drawn on FIG. 3. The selected radial line 60 is an estimate of a midpoint of the bright fan regions 50, 52.

In the example of FIG. 3, the imaging data sets from which the difference data set is formed are from a 4D sequence, and differ by about 20° of gantry rotation. The range of angles corresponding to non-overlapping times is brighter than other angles, with the approximate midpoint of the non-overlapping range of angles marked with line 60.

In the present embodiment, the midpoint is obtained automatically. In other embodiments, the difference data set may be displayed to a user, and the user may estimate the midpoint. In some circumstances, the difference data set image may be indistinct, and the angles may be determined by a user rather than automatically. In some circumstances, the determination of the angles may be crowdsourced as an alternative to determining the angles algorithmically.

Although in the present embodiment a midpoint of the non-overlapping angles is determined, in other embodiments any suitable gantry angle may be estimated: for example, a midpoint of a non-overlapping region, a midpoint of an overlapping region, or a boundary between an overlapping region and a non-overlapping region.

In other embodiments, any suitable method may be used to estimate one or more gantry rotation angles. The analysis circuitry 26 may use any suitable method to analyse differences between two 2D Fourier transformations of each slice to determine a range of radial angles corresponding to sinogram data that is not shared by the imaging data sets. The central slice theorem implies that radial lines at these angles are overall brighter than lines at angles corresponding to shared data.

The sum of squares method described above may be particularly useful in the case of imaging data sets for which the ranges of angles have a considerable overlap. In the example shown in FIG. 3, the first imaging data set and second imaging data set are reconstructed from ranges of angles that are offset by 20°. In some circumstances (for example, in some circumstances in which the offset is larger, for example 90°), the sum of squares method may perform more poorly.

In some embodiments, the analysis circuitry 26 fits a two-dimensional function to the difference data set. In some embodiments, the 2D function is based on a dipole radiation pattern. In some embodiments, the 2D function is a 2D Gaussian. The analysis circuitry 26 determines an angle of a principal axis of the fitted 2D function. The angle of the principal axis is used as an estimate of a midpoint of a non-overlapping range of angles.

In some embodiments, the analysis circuitry 26 determines a profile along a circular trajectory around the centre of the difference data set. The analysis circuitry 26 may smooth the resulting profile, for example to reduce effects of noise. The analysis circuitry 26 determines at least one peak in the determined profile. The analysis circuitry uses a position of a peak as an estimate of the midpoint of the non-overlapping range of angles. In some such embodiments, the analysis circuitry 26 may also use model fitting.

In some embodiments, the analysis circuitry 26 uses a Fourier transformation method inspired by the DART registration algorithm (see, for example, Maas, Frederick, Renshaw, Decoupled automated rotational and translational registration for functional MRI time series data: the DART registration algorithm, *Magnetic Resonance in Medicine,* 1997) to obtain an estimated angle. A profile is taken on a circular trajectory as described above. A spectral decomposition of this profile (for example, a spectral decomposition obtained by performing a one-dimensional Fourier transform) may be expected to have a dominant component corresponding to a sine wave with a 180° period. The phase of that sine wave may be related to the midpoint of the non-overlapping angle. If the phase of the sine wave is θ°, the midpoint may be at (θ+90°)/2.

In some embodiments, the analysis circuitry 26 estimates a line of reflective symmetry in the difference data set. The line of reflective symmetry may be a line of approximate reflective symmetry. The difference data set may not have exact reflective symmetry (although it may have exact 180° rotational symmetry). The analysis circuitry uses the line of reflective symmetry as an estimate of the midpoint of a non-overlapping region.

In other embodiments, any suitable method may be used to determine any appropriate angle of the first range of gantry rotation angles used in the reconstruction of the first imaging data set, or any appropriate angle of the second range of gantry rotation angles used in the reconstruction of the second imaging data set. For example, the analysis circuitry 26 may estimate an angle in an overlapping region, an angle in a non-overlapping region, or an angle on a boundary between an overlapping region and a non-overlapping region.

In the embodiment described in relation to FIG. 3, the first imaging data set and second imaging data set are representative of a single axial slice. In other embodiments, the first imaging data set and second imaging data set are representative of a plurality of axial slices.

In one embodiment, a first imaging data set comprises a reconstruction of several axial slices, each reconstructed from data for a first range of angles (for example, 0° to 180°).

A second imaging data set comprises a reconstruction of the same axial slices, each reconstructed from data for a second range of angles (for example, 90° to 270°).

A two-dimensional Fourier transform may be applied to each slice and a difference data set may be obtained by taking the difference of the transformed first imaging data set and the transformed second imaging data set. Data from a plurality of slices may be used in estimating an angle, for example for estimating a midpoint of a non-overlapping range of angles.

In some embodiments, each multiple-slice volume is treated as a single data set, but the DFT is computed separately on several slices of each volume. Once the DFTs are obtained, they are combined and the combination of the DFTs is used to determine a single range of angles.

Helical data sets may be treated differently, because each slice of a helical data set is acquired over a different range of angles. All slices of the helical data set may be considered to be related, but their angles may depend on z position instead of all being the same.

In some embodiments, multiple slices may be combined before transformation. However, in some circumstances, doing the transformation and difference slice-by-slice may give better results, because combining multiple slices first may tend to average out noise and fine detail, which may contribute to the differences that are present in the transformed data. Once the slices have been transformed, the resulting transformed images may be combined to reduce noise and improve robustness.

The process of FIG. 2 may be repeated for a plurality of axial slices representative of a patient. The process of FIG. 2 may be repeated for different data sets. The process of FIG. 2 may be repeated for any two or more imaging data sets that are representative of the same anatomy, for example two or more imaging data sets that are representative of a single axial slice.

The method of FIG. 2 has been described above for the simplest case of two imaging data sets. In some embodiments, the analysis circuitry 26 may obtain from two imaging data sets only the central angle from the non-overlapping data. However, knowledge of the central angle may be sufficient for some motion compensation methods. In other embodiments, the analysis circuitry 26 may obtain further information from two imaging data sets. For example, the analysis circuitry 26 may process the difference data set to obtain an estimate of a range of non-overlapping angles.

In some embodiments, angular information is obtained by processing three or more imaging data sets. For example, three or more imaging data sets may be processed to obtain a complete range of rotation angles for each of the three or more imaging data sets.

Consider the case in which three imaging data sets A, B, and C have been reconstructed from CT scan data representative of a single axial slice. Each of the imaging data sets has been reconstructed from CT scan data for a different range of gantry rotation angles. The offsets between the ranges of gantry rotation angles are such that the ranges of A and B overlap; the ranges of B and C overlap; and the ranges of A and C overlap.

The computing apparatus 12 performs the process of FIG. 2 on each pair of imaging data sets, A-B, A-C and B-C. The computing apparatus 12 determines a midpoint of a respective non-overlapping region for each pair A-B, A-C, B-C. The determined midpoints, and the knowledge that each imaging data set is reconstructed from a 180° range of data, may be used to obtain a complete range of rotation angles for all three imaging data sets by simple algebra. Once the midpoints are known, there may only be one combination of angular ranges that would result in those midpoints.

In some motion compensation methods, imaging data sets are reconstructed that have an offset of about 90°. For imaging data sets having an offset of 90°, it may not be possible to use three imaging data sets A, B and C to determine the full rotational ranges for three imaging data sets A, B, C by estimating for each pair A-B, A-C and B-C a midpoint of a respective non-overlapping region, since if A and B are 90° apart and B and C are 90° apart, A and C do not overlap.

In some embodiments, for example if there is no overlap between first and third images A and C, difference data sets for overlapping pairs of images (for example, A-B, B-C) may be used to determine a range of angles over which the Fourier transformations are significantly different. For example, the analysis circuitry 26 may determine a range of angles for each of the bright regions 50, 52. In some embodiments, finding a range of non-overlapping angles may be less robust than finding a midpoint of the range of non-overlapping angles. However, within a given acquisition, it may be possible to compute relative ranges consistently.

In some circumstances, tolerances of the angular estimation may be below 10° of angle. Lower tolerances may be used in some particular methods, for example in motion compensated reconstruction.

In some circumstances, additional information about the reconstruction may be used in the determination of one or more gantry angles. For example, even if the computing apparatus 12 does not have information about the gantry angles for the data used in each individual imaging data set, it may be known that consecutive imaging data sets are reconstructed from ranges that are 90° apart.

Figure 4A:
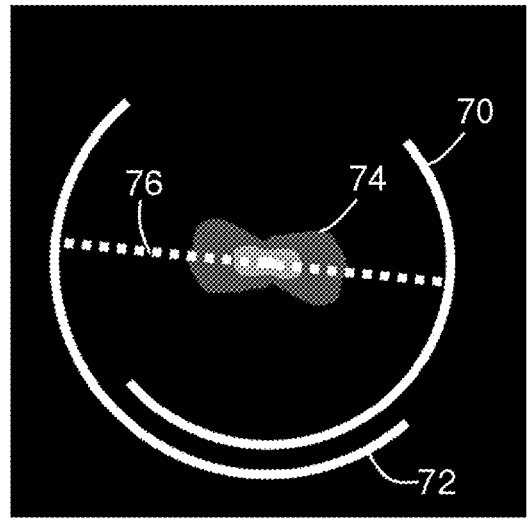
FIGS. 4a and 4b each show a schematic illustration of ranges of gantry angles for a pair of datasets, and a determined approximate principal angle.
Figure 4B:
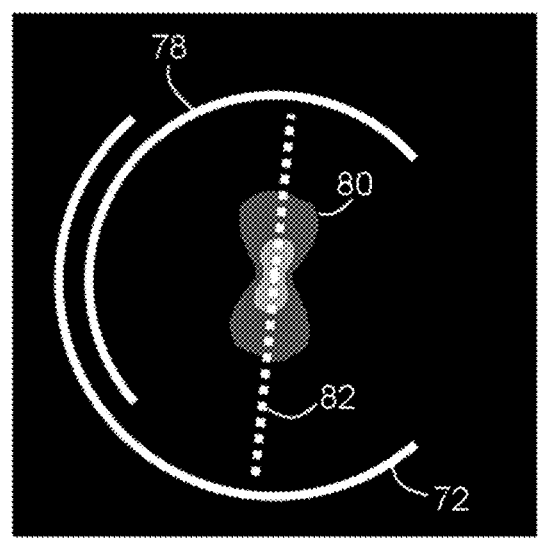

FIGS. 4a and 4b are schematic illustrations representing examples of estimation of a midpoint of a non-overlapping range obtained from real data. In the embodiment of FIGS. 4a and 4b, half-rotation reconstructions are spaced 90° apart.

Each of FIGS. 4a and 4b is representative of a sum of absolute differences of Fourier transformations over eight uniformly spaced slices, with some smoothing applied to the difference data set to improve robustness.

In FIG. 4a, line 70 is representative of a 180° range of ground truth gantry angles for a first imaging data set. Line 72 is representative of a 180° range of ground truth gantry angles for a second imaging data set.

A difference data set was obtained from the first imaging data set and second imaging data set using the method described above with reference to FIG. 2. A two-dimensional function 74 was fitted to the difference data set. Line 76 shows the approximate principal angle of the difference data set, determined from the fitting of the two-dimensional function.

The approximate principal angle obtained using the method of FIG. 2 was found to be a good estimate of the midpoint of the non-overlapping range of gantry angles (which can be seen from the ground truth ranges 70, 72).

In FIG. 4b, line 72 is representative of a range of a 180° ground truth gantry angles for a second imaging data set and line 78 is representative of a 180° range of ground truth gantry angles for a third imaging data set. A difference data set was obtained from the second imaging data set and third imaging data set using the method described above with reference to FIG. 2. A two-dimensional function 80 was fitted to the difference data set. Line 82 shows the approximate principal angle of the difference data set, determined from the fitting of the two-dimensional function.

Again, an approximate principal angle obtained using the method of FIG. 2 was found to be a good estimate of the midpoint of the non-overlapping range of gantry angles (which can be seen from the ground truth ranges 72, 78).

The method of FIG. 2 may provide a method of determining angles of gantry rotation automatically. For example, gantry rotation angles may be determined from imaging data sets that are supplied from the CT scanner 14 without associated gantry rotation angles being supplied. Gantry rotation angles may be determined for stored imaging data sets.

Angles obtained using the process of FIG. 2 may be used in motion estimation and/or motion compensated reconstruction. In some methods of motion estimation, cardiac motion may be estimated based on a number of reconstruction volumes (for example, three reconstruction volumes) that are representative of very close time points. See, for example, U.S. patent application Ser. No. 14/519,564. In order to estimate motion, a relative time (corresponding to a relative angle) between reconstruction volumes may be used. Different reconstruction volumes may be registered to each other in order to determine motion occurring between the reconstruction volumes.

In some embodiments, angles obtained using the process of FIG. 2 may be used to determine a relative angle between imaging data sets, and therefore to determine a relative time between imaging data sets. The computing apparatus 12 may use the relative time or angle in a motion estimation process to estimate motion between imaging data sets.

In some embodiments, angles obtained using the process of FIG. 2 may be used in motion compensated reconstruction. The computing apparatus 12 may create a new reconstruction of the data with reduced artifacts. For example, the computing apparatus 12 may register together a first and second imaging data sets corresponding to different scanning time periods. The computing apparatus 12 may use the registration to determine a motion estimate, for example a warp field. The computing apparatus 12 may reconstruct a further imaging data set using the estimated motion, for example by using the method of Tang et al, A combined local and global motion estimation and compensation method for cardiac CT, Proc. SPIE 9033, Medical Imaging 2014: Physics of Medical Imaging, 903304 (19 Mar. 2013).

For example the computing apparatus may divide an angular range of one of the imaging data sets into a plurality of regions (in one example, 12 regions of 15' each), obtain partial reconstructions of each of the regions, interpolate the motion estimation to a time of each of the plurality of regions, transform the partial reconstructions to incorporate the interpolated motion estimation, and combine the partial reconstructions to obtain a new imaging data set in which motion has been at least partially compensated.

In some embodiments, the computing apparatus 12 may perform motion estimation and/or motion compensated reconstruction without receiving gantry rotation angle information from the CT scanner 14, memory 20 or data store.

In some existing systems, motion compensation methods may be tightly integrated into a CT product (for example, a CT scanner) to make use of angular information available in the CT scanner.

A reconstruction stage of a motion compensation method may use knowledge of angles of gantry rotation for images to be corrected. Some motion estimation methods may also use this information.

The method of FIG. 2 may allow motion compensation methods (or other methods that use angular information) to be performed by a workstation that does not have access to angular information available in the scanner 14. The method of FIG. 2 may be performed by a standalone workstation.

Gantry angle information may not normally be available to a workstation that receives reconstructed data. By determining the angles of gantry rotation automatically from imaging data sets, motion estimation and/or motion compensation methods that use such angular information may be applied to imaging data sets.

Motion estimation and/or motion compensation methods may be applied to previously-acquired data, for example data that has been stored in a PACS system. In some circumstances, motion estimation and/or motion compensation methods may be applied to historic scan data which had been captured without contemplating its use in motion estimation and/or motion compensation. In some circumstances, new motion estimation and/or motion compensation techniques may be applied to data that was taken before the new motion estimation and/or motion compensation techniques became available.

The system of FIG. 1 may be used to estimate angular parameters related to CT scan data. By estimating gantry rotation angles from imaging data sets, it may become possible to apply some motion compensation methods to data where the angles are not otherwise recorded.

In further embodiments, angles obtained using the method of FIG. 2 may be used in applications other than motion estimation and/or motion reconstruction. The angles may be used as input to any suitable algorithm. For example, in some embodiments, angles estimated using the method of FIG. 2 are used in a process of metal artifact reduction. In some circumstances, artifacts in an image caused by a metal object (for example, a dental filling, orthopedic plate, or spinal rod) may differ in dependence on the angles of rotation of the data used to reconstruct the image. For example, X-rays may be scattered more when striking the metal object from a particular angle. In some embodiments, estimating angles from imaging data sets may allow the imaging data set having the lowest level of metal artifacts to be selected. In some embodiment, estimated angles may be used to perform a method of removing or reducing metal artifacts.

Embodiments describes above are embodiments in which a scanner gantry rotates around a patient or other subject. In other embodiments, a source and/or receiver may remain static while a patient or other subject is rotated. In such embodiments, the method of FIG. 2 may be used to determine at least one angle of rotation of the patient. In general, the angles determined may be angles of relative rotation of at least part of a scanner and at least part of a patient or other subject.

In the present embodiment, the scanner acquires CT data and reconstructs that CT data to provide imaging data. In other embodiments, the scanner acquires data of any suitable modality (for example, CT, cone-beam CT, MR, PET, SPECT, X-ray or ultrasound) and uses a reconstruction method suitable for reconstructing imaging data sets from data of the acquired modality. The scanner may reconstruct data from the scanner to provide any appropriate two-dimensional or three-dimensional imaging data sets. In some embodiments, the scanner is a cone-beam CT scanner. In some embodiments, the imaging data sets are angiography imaging data sets.

The measurement volume may be any appropriate anatomical region of any human or animal subject. The anatomical region may comprise any suitable anatomical structure, for example any organ (for example, heart, lung or liver) or vessel (for example, coronary artery). The anatomical region may be a region that is subject to motion (for example, heart motion). The anatomical region may be a region for which it is desired to perform motion estimation and/or motion compensation.

Certain embodiments provide a medical imaging method comprising receiving two or more 2D or 3D CT image datasets of a given portion of a patient, each dataset reconstructed from sinogram data over a given period, such that the time periods of at least one pair of datasets overlap, and for at least one pair of image datasets, determining the midpoint and/or duration of the range of time periods for the first dataset that do not overlap with the time period of the second dataset.

The determining of the midpoint and/or duration may comprise:
a) computing the 2D discrete Fourier transformation (DFT) of each image of each of the pair of datasets;
b) computing the difference of the two DFTs computed in step a); and
c) determining the midpoint and/or size of the range of angles over which the difference computed in step b) has largest magnitude.

Step c) may comprise computing the sum of squares along many radial lines through the centre of the difference image, and returning the angle at which the sum of squares is largest.

Certain embodiments may provide a medical imaging method comprising: receiving three or more 2D or 3D CT image datasets of a given portion of a patient, each dataset reconstructed from sinogram data over a given time period, such that the time periods of at least one pair of datasets overlap; for at least two pairs of image datasets, determining the range of time periods for the first dataset that do not overlap with the time period of the second dataset; and using the information from the determining of the range of time periods, determining the full range of angles of CT gantry rotation for each of the datasets received.

Certain embodiments provide a method for correcting motion artifacts in CT image datasets, comprising: receiving three or more 3D CT image datasets of a given portion of a patient; estimating anatomical motion between at least two pairs of the datasets; determining the range of angles of CT gantry rotation for each of the datasets; and using the estimated anatomical motion and determined range of angles in reconstructing a further CT image dataset with reduced motion artifacts.

Whilst particular circuitries have been described herein, in alternative embodiments functionality of one or more of these circuitries can be provided by a single processing resource or other component, or functionality provided by a single circuitry can be provided by two or more processing resources or other components in combination. Reference to a single circuitry encompasses multiple components providing the functionality of that circuitry, whether or not such components are remote from one another, and reference to multiple circuitries encompasses a single component providing the functionality of those circuitries.

Whilst certain embodiments have been described, these embodiments have been presented by way of example only, and are not intended to limit the scope of the invention. Indeed the novel methods and systems described herein may be embodied in a variety of other forms; furthermore, various omissions, substitutions and changes in the form of the methods and systems described herein may be made without departing from the spirit of the invention. The accompanying claims and their equivalents are intended to cover such forms and modifications as would fall within the scope of the invention.

The invention claimed is:

1. A medical imaging data processing apparatus comprising:
   processing circuitry configured to:
      obtain a first imaging data set comprising a set of pixels or voxels, the first imaging data set being reconstructed from first measurement data representative of measurements of a measurement volume obtained by relative rotation of a medical scanner and the measurement volume by a first range of angles during a first scanning time period;
      obtain a second imaging data set comprising a set of pixels or voxels, the second imaging data set being reconstructed from second measurement data representative of measurements of the measurement volume obtained by relative rotation of the medical scanner and the measurement volume by a second range of angles during a second scanning time period, wherein the second scanning time period overlaps the first scanning time period such that some angles are included in both the first range of angles and the second range of angles;
      transform the first imaging data set to obtain a first transformed data set that is representative of the first measurement data as a function of at least one of angle or time;
      transform the second imaging data set to obtain a second transformed data set that is representative of the second measurement data as a function of at least one of angle or time; and
      determine at least one angle of the first range of angles and/or second range of angles based on differences between the first transformed data set and second transformed data set by comparing pixel values of the first transformed data set to corresponding pixel values of the second transformed data set.

2. The apparatus according to claim 1, wherein the processing circuitry determines the at least one angle by:
   obtaining a difference data set representative of the differences between the transformed first data set and transformed second data set; and
   obtaining the estimate of the at least one angle based on the difference data set.

3. The apparatus according to claim 2, wherein the processing circuitry obtains the difference data set by subtracting the transformed first data set and transformed second data set.

4. The apparatus according to claim 1, wherein the processing circuitry transforms by applying to each of the first imaging data set and second imaging data set at least one of: a Fourier transform, a discrete Fourier transform, a Fast Fourier transform, a number-theoretic transform, a discrete weighted transform, a Chirp Z-transform.

5. The apparatus according to claim 2, wherein the processing circuitry is further configured to apply a logarithm operator to the difference data set.

6. The apparatus according to claim 1, wherein the at least one angle comprises a midpoint and/or a boundary of a non-overlapping range of angles that are included in one of the first range of angles and second range of angles but not in the other of the first range of angles and second range of angles.

7. The apparatus according to claim 1, wherein the at least one angle comprises a midpoint and/or a boundary of an overlapping range of angles that are included in both the first range of angles and the second range of angles.

8. The apparatus according to claim 1, wherein the at least one angle comprises at least one boundary of the first range of angles and/or at least one boundary of the second range of angles.

9. The apparatus according to claim 2, wherein the processing circuitry determines the at least one angle based on a magnitude of elements of the difference data set.

10. The apparatus according to claim 2, wherein the processing circuitry determines the at least one angle of rotation by at least one of a) to e):
   a) determining a respective sum of squares for each of a plurality of radial lines through the difference data set;
   b) fitting a two-dimensional function to the difference data set;
   c) determining a profile along a circular trajectory around the centre of the difference data set;
   determining a profile along a circular trajectory around the centre of the difference data set and obtaining a spectral decomposition of the profile;
   e) determining an angle of a line of reflective symmetry of the difference data set.

11. The apparatus according to claim 1, wherein the processing circuitry is further configured to obtain an estimate of motion between the first imaging data set and second imaging data set using the determined at least one angle.

12. The apparatus according to claim 11, wherein the processing circuitry is further configured to perform motion compensated reconstruction using the estimate of motion.

13. The apparatus according to claim 1, wherein the processing circuitry is further configured to:
   obtain a third imaging data set comprising a set of pixels or voxels, the third imaging data set being reconstructed from third measurement data representative of measurements of the measurement volume obtained by relative rotation of the medical scanner and the measurement volume by a third range of angles during a third scanning time period, wherein the third scanning time period overlaps each of the first and second scanning time periods;
   transform the third imaging data set to obtain a third transformed data set that is representative of the third measurement data as a function of at least one of angle or time; and
   obtain an estimate of boundaries of the first range of angles, second range of angles and third range of angles based on the first transformed data set, second transformed data set and third transformed data set.

14. The apparatus according to claim 1, wherein the processing circuitry determines the at least one angle by estimating said at least one angle.

15. The apparatus according to claim 1, wherein the measurement volume comprises an anatomical region of a subject.

16. The apparatus according to claim 15, wherein the anatomical region comprises at least one of a vessel, a coronary artery, an organ, a heart, a lung, a liver.

17. The apparatus according to claim 14, wherein the measurement volume comprises at least one metal object.

18. The apparatus according to claim 1, wherein the medical scanner comprises at least one of a CT scanner, a cone-beam CT scanner, an MRI scanner, a PET scanner, a SPECT scanner, an X-ray scanner, an ultrasound scanner.

19. A medical imaging data processing method comprising:
   obtaining a first imaging data set comprising a set of pixels or voxels, the first imaging data set being reconstructed from first measurement data representative of measurements of a measurement volume obtained by relative rotation of a medical scanner and the measurement volume by a first range of angles during a first scanning time period;
   obtaining a second imaging data set comprising a set of pixels or voxels, the second imaging data set being reconstructed from second measurement data representative of measurements of the measurement volume obtained by relative rotation of the medical scanner and the measurement volume by a second range of angles during a second scanning time period, wherein the second scanning time period overlaps the first scanning time period such that some angles are included in both the first range of angles and the second range of angles;
   transforming the first imaging data set to obtain a first transformed data set that is representative of the first measurement data as a function of at least one of angle or time;
   transforming the second imaging data set to obtain a second transformed data set that is representative of the second measurement data as a function of at least one of angle or time; and
   determining at least one angle of the first range of angles and/or second range of angles based on differences between the first transformed data set and second transformed data set by comparing pixel values of the first transformed data set to corresponding pixel values of the second transformed data set.

20. A computer program product comprising a computer readable memory storing instructions that are executable to perform a method, the method comprising:
   obtaining a first imaging data set comprising a set of pixels or voxels, the first imaging data set being reconstructed from first measurement data representative of measurements of a measurement volume obtained by relative rotation of a medical scanner and the measurement volume by a first range of angles during a first scanning time period;
   obtaining a second imaging data set comprising a set of pixels or voxels, the second imaging data set being reconstructed from second measurement data representative of measurements of the measurement volume obtained by relative rotation of the medical scanner and the measurement volume by a second range of angles during a second scanning time period, wherein the second scanning time period overlaps the first scanning time period such that some angles are included in both the first range of angles and the second range of angles;

transforming the first imaging data set to obtain a first transformed data set that is representative of the first measurement data as a function of at least one of angle or time;

transforming the second imaging data set to obtain a second transformed data set that is representative of the second measurement data as a function of at least one of angle or time; and determining at least one angle of the first range of angles and/or second range of angles based on differences between the first transformed data set and second transformed data set by comparing pixel values of the first transformed data set to corresponding pixel values of the second transformed data set.

* * * * *